(12) United States Patent
Römisch et al.

(10) Patent No.: US 7,879,803 B2
(45) Date of Patent: Feb. 1, 2011

(54) METHODS OF TREATMENT INVOLVING THE PROTEASE FOR ACTIVATING CLOTTING FACTOR VII

(75) Inventors: Jürgen Römisch, Marburg (DE); Annette Feussner, Marburg (DE); Hans-Arnold Stöhr, Wetter (DE)

(73) Assignee: CSL Behring GmbH, Marburg (DE)

( * ) Notice: Subject to any disclaimer, the term of this patent is extended or adjusted under 35 U.S.C. 154(b) by 258 days.

(21) Appl. No.: 11/984,058

(22) Filed: Nov. 13, 2007

(65) Prior Publication Data
US 2008/0175878 A1 Jul. 24, 2008

Related U.S. Application Data

(62) Division of application No. 11/118,396, filed on May 2, 2005, now abandoned, which is a division of application No. 10/319,592, filed on Dec. 16, 2002, now Pat. No. 6,911,334, which is a division of application No. 09/295,316, filed on Apr. 21, 1999, now Pat. No. 6,528,299.

(30) Foreign Application Priority Data

| Apr. 24, 1998 | (DE) | ................................. 198 18 495 |
| Jun. 22, 1998 | (DE) | ................................. 198 27 734 |
| Nov. 6, 1998 | (DE) | ................................. 198 51 332 |
| Nov. 6, 1998 | (DE) | ................................. 198 51 335 |
| Nov. 6, 1998 | (DE) | ................................. 198 51 336 |
| Feb. 1, 1999 | (DE) | ................................. 199 03 693 |

(51) Int. Cl.
*A61K 38/00* (2006.01)

(52) U.S. Cl. ..................... 514/14.3; 514/13.7; 514/14.6; 514/14.9

(58) Field of Classification Search ........................ None
See application file for complete search history.

(56) References Cited

U.S. PATENT DOCUMENTS

| 4,363,319 | A | * | 12/1982 | Altshuler ..................... 604/304 |
| 4,447,412 | A | * | 5/1984 | Bilton ........................ 424/498 |
| 5,175,087 | A | | 12/1992 | Ranby et al. |
| 5,580,859 | A | * | 12/1996 | Felgner et al. ............. 514/44 R |
| 6,359,054 | B1 | * | 3/2002 | Lemieux et al. ............. 524/505 |
| 6,528,299 | B1 | | 3/2003 | Roemisch et al. |
| 7,153,679 | B2 | * | 12/2006 | Kiechl et al. ................. 435/226 |
| 2002/0110552 | A1 | | 8/2002 | Roemisch et al. |
| 2003/0077271 | A1 | | 4/2003 | Roemisch et al. |
| 2003/0124622 | A1 | | 7/2003 | Roemisch et al. |
| 2003/0215447 | A1 | | 11/2003 | Roemisch et al. |
| 2004/0063187 | A1 | | 4/2004 | Roemisch et al. |
| 2004/0186277 | A1 | | 9/2004 | Roemisch et al. |
| 2005/0032109 | A1 | | 2/2005 | Roemisch et al. |

FOREIGN PATENT DOCUMENTS

| FR | 2 504 921 | 5/1982 |
| WO | WO 91/01497 | 2/1991 |
| WO | WO 9306855 A1 * | 4/1993 |
| WO | WO 96/10638 | 4/1996 |

OTHER PUBLICATIONS

Kazama, Yoshiaki et al., "Hepsin, a Putative Membrane-Associated Serine Protease, Activates Human Factor VII and Initiates a Pathway of Blood Coagulation on the Cell Surface Leading to Thrombin Formation," *The Journal of Biological Chemistry*, vol. 270 (1), pp. 66-72, (1995).
Choi-Miura, Nam-Ho et al., "Purification and Characterization of a Novel Hyaluronan-Binding Protein (PHBP) From Human Plasma: It Has Three EGF, a Kringle and a Serine Protease Domain, Similar to Hepatocyte Growth Factor Activator," *J. Biochem*, vol. 119 (6), pp. 1157-1165 (1996).
Laake, K. et al., "Activation of Purified Plasma Factor VII by Human Plasmin, Plasma Kallikrein, And Activated Components of the Human Intrinsic Blood Coagulation System," *Thrombosis Research*, vol. 5 (6), pp. 759-772 (1974).
Römisch, J. et al., "A Protease Isolated From Plasma Which Activates FVII in a Tissue Factor Independent Manner But Inactivates FV and FVII I," Annals of Hematology, vol. 78 (1), pp. 24-27 (1999) (Abstract).
Römisch, J. et al., "The FVII Activating Protease Mediates Fibrinolytic Effects Activating Single-Chain Plasminogen Activators," *Annals of Hematology*, vol. 78 (1), pp. 24-27 (1999) (Abstract).
Hunfeld, A. et al., "Identification of the Thrombin-Like Activity of PCCs," *Annals of Hematology*, vol. 76 (1), pp. 25-28 (1998) (Abstract).
Etscheid et al., 43$^{rd}$ Annual Meeting of the GTH; Supplement 1 to vol. 78 A42, P030 (1999).
Hunfeld et al., 42$^{nd}$ Annual Meeting of the GTH; Supplement 1 to vol. 76 A101, P294 (1998).
Hunfeld et al., 41$^{st}$ Annual Meeting of the GTH; Supplement 1 to vol. 74 A87 P113 (1997).
Römisch et al., 43$^{rd}$ Annual Meeting of the GTH; Supplement 1 to vol. 78 A24, FV079 (1999).
Römisch et al., 43'd Annual Meeting of the GTH; Supplement 1 to vol. 78 A10, FV024 (1999).
Hirsh et al., "Heparin and low-molecular-weight heparin: mechanisms of action, pharmacokinetics, dosing information, monitoring, efficacy, and safety," *Chest* 114(Suppl. 5): 489S-510S (1998).
N. Kitamura, GenBank accession D49742 (1995).
K. Hashimoto et al., "Cloning of the cDNA for a Mouse Homologue of Human PHBP: a Novel HyaluronanBinding Protein," *Biol. Pharm. Bulletin*, vol. 20 (11): 1127-1130 (1997).

(Continued)

*Primary Examiner*—Michael Szperka
(74) *Attorney, Agent, or Firm*—Finnegan, Henderson, Farabow, Garrett & Dunner, LLP (57) ABSTRACT

This application describes methods of treatment involving a protease for activating the blood clotting factor VII, which (a) activates blood clotting factor VII, (b) is inhibited by the presence of aprotinin, (c) is increased in its activity by the presence of at least one of the following: calcium ions, heparin, or heparin related substances, and (d) in SDS-PAGE, on subsequent staining in the non-reduced state, has one or more bands in the molecular weight range from 50 to 75 kDa, and in the reduced state has a band at 40 to 55 kDa and one or more bands in the molecular weight range from 10 to 35 kDa, and a band, which corresponds to a proenzyme, in the molecular weight range from 60 to 65 kDa.

13 Claims, 3 Drawing Sheets

OTHER PUBLICATIONS

J-I. Sumiya et al., "Isolation and Characterization of the Plasma Hyaluronan-Binding Protein (PHBP) Gene (*HABP2*)," *J. Biochem.*, vol. 122: 983-990 (1997).

A. Zhukov et al., "Purification and characterization of hepsin from rat liver microsomes," *Biochimica et Biophysica Acta*, vol. 1337: 85-95 (1997).

A. Hunfeld et al., "Detection of a novel plasma serine protease during purification of vitamin K-dependent coagulation factors," *FEBS Letters*, vol. 1 (456): 290-294 (1999).

J. Roemisch et al., "A Protease Isolated From human plasma activating Factor VII independent of tissue factor," *Blood Coagulation and Fibrinolysis*, vol. 10 (8): 471-479 (1999).

A. Vostrov et al., "Plasma Hyaluronan-binding Protein Is a Serine Protease," *J. Biological Chemistry*, vol. 275 (30): 22978-22985 (2000).

J. Roemisch et al., "Factor VII Activating Protease (FSAP): A Novel Protease in Hemostasis," *Biol. Chem.*, 383: 1119-1124 (2002).

* cited by examiner

SEQUENCE LISTING

<160> NUMBER OF SEQ ID NOS: 6

<210> SEQ ID NO 1
<211> LENGTH: 11
<212> TYPE: PRT
<213> ORGANISM: Unknown

-continued

```
<220> FEATURE:
<223> OTHER INFORMATION: Description of Unknown Organism: Illustrative
      peptide

<400> SEQUENCE: 1

Ile Tyr Gly Gly Phe Lys Ser Thr Ala Gly Lys
1               5                   10

<210> SEQ ID NO 2
<211> LENGTH: 10
<212> TYPE: PRT
<213> ORGANISM: Unknown
<220> FEATURE:
<223> OTHER INFORMATION: Description of Unknown Organism: Illustrative
      peptide

<400> SEQUENCE: 2

Ile Tyr Gly Gly Phe Lys Ser Thr Ala Gly
1               5                   10

<210> SEQ ID NO 3
<211> LENGTH: 12
<212> TYPE: PRT
<213> ORGANISM: Unknown
<220> FEATURE:
<223> OTHER INFORMATION: Description of Unknown Organism: Illustrative
      peptide

<400> SEQUENCE: 3

Ile Tyr Gly Gly Phe Lys Ser Thr Ala Gly Lys His
1               5                   10

<210> SEQ ID NO 4
<211> LENGTH: 7
<212> TYPE: PRT
<213> ORGANISM: Unknown
<220> FEATURE:
<223> OTHER INFORMATION: Description of Unknown Organism: Illustrative
      peptide

<400> SEQUENCE: 4

Leu Leu Glu Ser Leu Asp Pro
1               5

<210> SEQ ID NO 5
<211> LENGTH: 4
<212> TYPE: PRT
<213> ORGANISM: Unknown
<220> FEATURE:
<223> OTHER INFORMATION: Description of Unknown Organism: Illustrative
      peptide

<400> SEQUENCE: 5

Ser Leu Asp Pro
1

<210> SEQ ID NO 6
<211> LENGTH: 12
<212> TYPE: PRT
<213> ORGANISM: Unknown
<220> FEATURE:
<223> OTHER INFORMATION: Description of Unknown Organism: Illustrative
      peptide

<400> SEQUENCE: 6

Ser Leu Leu Glu Ser Leu Asp Pro Trp Thr Pro Asp
1               5                   10
```

METHODS OF TREATMENT INVOLVING THE PROTEASE FOR ACTIVATING CLOTTING FACTOR VII

This application is a division of application Ser. No. 11/118,396 file on May 2, 2005 now abandoned, which is a division of application Ser. No. 10/319,592 file Dec. 16, 2002, now U.S. Pat. No. 6,911,334, which is a division of application Ser. No. 09/295,316, filed Apr. 21, 1999, now U.S. Pat. No. 6,528,299. This application also claims priority to German Application Nos. 198 18 495, filed Apr. 24, 1998, 198 27 734, filed Jun. 22, 1998, 198 51 332, filed Nov. 6, 1998, 198 51 335, filed Nov. 6, 1998, 198 51 336, filed Nov. 6, 1998, and 199 03 093, filed Feb. 1, 1999. All of the above applications are incorporated in their entirety by reference herein.

DESCRIPTION OF THE INVENTION

1. Field of the Invention

The invention relates to a protease for activating the blood clotting factor V11, to a process for isolating it, detecting it and inactivating it, and to medicinal preparations which comprise this protease.

2. Background of the Invention

The blood clotting system comprises two different, cascade-like pathways for activating clotting factors which are present in the plasma. The intrinsic or the extrinsic pathway is preferentially used for initiating clotting, depending on the triggering mechanism.

When a tissue is damaged, thromboplastin (tissue factor, TF with phospholipids) is exposed by the affected cells as the starter of the extrinsic clotting pathway. The membrane-located thromboplastin can bind both clotting factor VII (FVII) and circulating, activated FVII (FVIIa). In the presence of calcium ions and lipids, this TF-FVIIa complex leads to the binding of FX, which is converted into its activated form (FXa) by limited proteolysis. FXa in turn leads, by activating prothrombin to form thrombin, to the formation of fibrin and thereby ultimately to closure of the wound.

While the further activation of the thromboplastin-bound FVII initially takes place autocatalytically, in particular, it is supported, after the clotting cascade has been initiated, by FXa and thrombin, in particular, leading to marked reinforcement of the reaction cascade.

The administration of FVIIa or FVIIa-containing concentrates is indicated in certain clinical situations. The so-called FVIII-bypassing activity (FEIBA) of FVIIa is used in patients who are suffering, for example, from hemophilia A and have developed antibodies against FVIII as a consequence of the administration of FVIII. According to presently available findings, FVIIa is well tolerated in this context and, while it does not lead to any tendency to thrombosis, it is suitable for ensuring that clotting takes place to a limited but adequate extent. Recombinant FVIIa is already being used therapeutically and prophylactically. FVII which has been isolated from blood plasma can also be activated and then used. Proteases such as thrombin can be used for this activation; however, these proteases, as such, can themselves strongly activate clotting and lead to the risk of a thrombosis. For this reason, subsequent removal or inactivation of thrombin is necessary and leads to yield losses. As a result of the risk of thrombosis which is associated with it, the use of FXa or FIIa (thrombin) is frequently contraindicated and only indicated in emergencies, e.g. in association with extreme loss of blood and unstaunchable hemorrhages.

FVIIa is found in very low concentrations in the plasma of healthy subjects. Only very little is so far known about the formation and origin of FVIIa which is circulating in the blood. Traces of thromboplastin which has been expressed or released in association with cell destruction might play a role in this context. Although it is known that factor XIIa, for example, can lead to FVII activation under certain conditions, the physiological relevance of this reaction has not yet been clarified.

Surprisingly, a FVII-activating protease, which differs from all the previously known proteases, has now been found in connection with fractionating human plasma and certain prothrombin complex concentrates. Investigations into this protease have shown that it exhibits a particularly high amidolytic activity toward the peptide substrate S2288 (HD-isoleucyl-L-prolyl-L-arginine-pNA) from Chromogenix AB, Sweden. A particular feature of this protease is that the amidolytic activity is efficiently inhibited by aprotinin. Other inhibitors, such as the antithrombin III/heparin complex, are also suitable for the inhibition. On the other hand, its activity is increased by heparin and heparin-related substances such as heparan sulfate or dextran sulfate and calcium ions. Finally, it has been found that this protease is able, in a manner dependent on time and on its concentration, to convert FVII into FVIIa. This reaction, too, is inhibited by aprotinin.

Part of the subject matter of the invention is therefore a protease for activating the blood clotting factor VII, which
  a) is inhibited by the presence of aprotinin,
  b) is increased in its activity by calcium ions and/or heparin or heparin-related substances, and
  c) in SDS-PAGE, on subsequent staining in the non-reduced state, has one or more bands in the molecular weight range from 50 to 75 kDa and kDa in the reduced state has a band at 40 to 55 kDa and one or more bands in the molecular weight range from 10 to 35 kDa.

In the following text, the activated form of the protease is termed "protease" whereas the non-activated form is termed "proenzyme".

Further investigations with this protease have shown that, after enriching or isolation, it suffers from a rapid loss of activity, which was observed in a solution containing 20 mM tris, 0.15 M NaCl at a pH of 7.5. The addition of albumin at a concentration of 0.1% was not able to prevent the activity of the protease from decreasing by 50% after one hour at room temperature. On the other hand, very good stabilization of the protease was observed in a solution which was buffered to a pH of 6.5 with 50 mM Na citrate. If no particular stabilizers are added to the protease solution, no, or only slight, losses in activity are observed if the solution is adjusted to a pH of between 4 and 7.2, preferably to a pH of between 5.0 and 7.0. However, it is expedient to add stabilizers to the solution, with suitable stabilizers, apart from citrate, being, in particular, glutamate, amino acids, such as arginine, glycine or lysine, calcium ions and sugars such as glucose, arabinose or mannose in quantities of 1-200 mmol/l, preferably in quantities of 5-100 mmol/l. Efficient stabilization was also achieved by adding glycols such as ethylene glycol or glycerol, with quantities of 5-80% by weight, preferably of 10-60% by weight, being used. The pH of the stabilized solution should then be between the pH values 4-9.

While the novel protease, and also the proenzyme, can be obtained by recombinant DNA methods or by production in e.g. the milk of suitable transgenic animals, they can in particular be obtained by fractionation of blood plasma or of prothrombin complex (PPSB) concentrates. The starting material is then first of all subjected to an anion exchange chromatography, which is followed by an affinity chromatography of the eluate. A heparin which is immobilized on a matrix, or a heparin-related substance such as heparan sulfate or dextran sulfate, is particularly suitable for the affinity chromatography. When such a chromatographic method is used, the novel protease and/or the proenzyme can be selectively found and then eluted once again using known methods. The use of a spacer is advisable for coupling the ligand to the matrix. A heparin-lysine matrix has been found to be particularly suitable for isolating the novel protease.

In SDS-PAGE with subsequent staining, the protease which has been isolated by this method exhibits, in the non-reduced state, one to several bands which lie closely together in the molecular weight range of 55-75 kDa. Following reduction, one to several bands were observed in the molecular weight range of 15-35 kDa and one band was observed at 40-55 kDa. A further band between 60 and 65 kDa, which, after scanning and quantitative evaluation, constituted 5-10% of the total protein, showed that non-activated proenzyme was also present. This result was supported by appropriate investigations using monoclonal antibodies against this protease. It was therefore concluded that the proenzyme of this protease can also be prepared, pasteurized and used by the method according to the invention. Part of the subject matter of the invention is therefore the proenzyme of the protease for activating blood clotting factor VII. The proportion of the proenzyme is indicated by the band between 60 and 65 kDa. Corresponding to the amino acid sequence which constitutes the activation region of the proenzyme, thrombin, kallikrein or FXIIa are, in accordance with their substrate specificities, examples of suitable physiological activators of the proenzyme.

Some of the properties of the novel protease which have been described, namely the fact that it can be isolated from plasma or from prothrombin complex (PPSB) concentrates which are derived from plasma, the inhibition of its amidolytic activity by aprotinin and the described migration behavior in SDS-PAGE, both in the reduced and in the non-reduced states, are reminiscent of a protease which was isolated by Hunfeld et al. (Ann. Hematol. 1997; 74; A87, 113; Ann. Hematol. 1998; 76; A101, P294 and Etscheid et al. Ann. Hematol. 1999, 78: A42) from a PPSB concentrate which was not defined in any more detail. In that case, the preparation was essentially achieved using an aprotinin matrix. As a result of the amidolytic cleavage of certain peptide substrates, the activity was described as being a thrombin-like activity. Hunfeld et al. did not find any influence on global clotting parameters such as prothrombin time, Quick or platelet aggregation.

The N-terminal sequencing of the protease described by Hunfeld et al. shows concordances with a protein whose cDNA was described by Choi-Miura et al. (J. Biochem. 119: 1157-1165 (1996)). In its primary structure, the corresponding protein exhibits homology with an enzyme termed hepatocyte growth factor activating enzyme (HGFA).

When two bands which were isolated from SDS-PAGE under reducing conditions were subjected to N-terminal sequencing, the following concordances were established:

| Molecular weight range of the band | Amino acid sequence | Author |
|---|---|---|
| 10-35 kDa | IYGGFKSTAGK | present invention |
| 30 kDa | IYGGFKSTAG | Hunfeld et al. |
| 17 kDa | IYGGFKSTAGKH | Choi-Miura et al. |
| 40-55 kDa | LLESLDP | present invention |
| 50 kDa | SLDP | Hunfeld et al. |
| 50 kDa | SLLESLDPWTPD | Choi-Miura et al. |

In the table above, the sequence IYGGFKSTAGK is SEQ ID NO. 1; the sequence IYGGFKSTAG is SEQ ID NO. 2; the sequence IYGGFKSTAGKH is SEQ ID NO. 3; the sequence LLESLDP is SEQ ID NO. 4; the sequence SLDP is SEQ ID NO. 5; and the sequence SLLESLDPWTPD is SEQ ID NO. 6.

Concordances are also found in other test results such as substrate specificity and the ability of the activity to be inhibited. Despite this, it is still not possible at present to assume with confidence that these proteins are identical. At any rate, the previously investigated, abovementioned proteins have not been reported to possess the property of activating FVII or activating other factors (see below).

On the basis of its described properties, the novel protease can be used diagnostically and therapeutically.

1. TEST SYSTEMS USING THE NOVEL PROTEASE

The novel protease can be used diagnostically in test reagents. Thus, the presence of factor VII can be determined qualitatively and quantitatively in a clotting test by adding the novel protease.

Conversely, the test system developed for measuring FVII activation can also be used for detecting and quantifying the protease. For this, a solution containing the protease is mixed with an FVII-containing solution and, after an appropriate incubation time, the resulting quantity of FVIIa is quantified. This can be carried out, for example, using the Staclot® FVIIa-rTF test (Stago/Boehringer Mannheim). When a preferred procedure is used, this test is not limited by the FVII concentration supplied. If the quantity of protease in the form of the proportion of total protein is known, which proportion can be determined in a pure protease preparation, by means of the Kjeldahl method or by means of another protein assay with which the skilled person is familiar, or using an antigen test, for example based on specific antibodies and an appropriate immunochemical determination method such as ELISA, the specific activity of the protease preparation can then be measured in a corresponding manner.

Surprisingly, a property has now been found, in association with characterizing the protease further, which makes it possible to carry out an additional determination method. In association with incubation of the blood clotting factors VIII/VIIIa and V/Va with said protease, and subsequent quantification, it became clear that said clotting factors are inactivated in a manner which is dependent on the protease concentration and on the length of the incubation.

Another part of the subject matter of the invention is therefore a novel test system for qualitatively and quantitatively detecting the protease which activates blood clotting factor VII, in which system the protease can be determined by its action inactivating the blood clotting factors VIII/VIIIa or V/Va. This test system is based on a solution containing the protease being incubated with factor VII/VIIa or factor V/Va and the remaining quantity of factor VII/VIIIa or the remaining quantity of factor V/Va being measured by means of a conventional activity test and the amount of protease then being quantitatively determined from this by comparison with a standard curve. In carrying out this test, the incubation of the protease activity is inhibited, after predetermined periods of time, by the limited addition of aprotinin, which has the advantage that it has no effect, at these concentrations, on the subsequent measurements of the test system. After that, the remaining activities of the clotting factors are measured by means of a test which is familiar to the skilled person. For this, a test system has, in particular, proved its worth in which use is made of the so-called Coamatic$^3$ factor VIII test (Chromogenix AB), which essentially contains factors IXa and X, with the resulting amount of FXa being quantified, in the presence of a thrombin inhibitor, by means of the conversion of a chromogenic substrate (see paragraph 7). This amount is in turn proportional to the quantity of FVIIII or FVIIIa. Determining the residual FVIII activity then makes it possible to deduce the concentration of protease which is present.

The degradation of the FVIII/FVIIIa or the FV/FVa due to the proteolytic effect can be clearly demonstrated by SDS-PAGE. Depending on the time for which the protease is incubated, for example, with an FVIII concentrate, bands which are typical for FVIII disappear while other, new bands emerge or weak bands increase in intensity. Accordingly, the activity of the protease can also be correlated by quantifying the decreasing or increasing bands and consequently measured quantitatively, for example using a protease standard. The changes in the band intensities on the SDS-PAGE electropherogram or following other electrophoretic methods can be quantified, for example, using a scanner, with which a skilled person is familiar, and the appropriate program. In addition to this, antibodies against said clotting factors can be used for Western blotting and employed for evaluation in the manner described. Antibodies which specifically detect the decreasing bands or, in particular, the emerging bands are particularly suitable. In this context, these antibodies can also be used for establishing other immunochemical tests such as an ELISA.

The proteolytic inactivation which has been described in the case of FVIII/FVIIIa is also observed when the protease is incubated with factor V/Va, which exhibits a certain degree of structural homology with FVIII. The degradation can be monitored in suitable activity test systems and in SDS-PAGE/Western blotting.

Despite the inactivations of FV and FVIII, it was now found that adding the protease to blood, to platelet-rich plasma or plasma shortened the clotting times, that is the procoagulatory effect predominated in various so-called "global clotting tests." These test systems are understood as being, for example, the non-activated partial thromboplastin time (NAPTT), the prothrombin time (PT) and the recalcification time. Since the shortening of these times, as measured, for example, in so-called coagulometers, by means of thromboelastography or else in chromogenic tests, correlates with the concentration of a clotting-promoting substance, the concentration of the substance in a sample can conversely be deduced using a calibration curve of the clotting time. The concentration of the "FVII activator" can correspondingly be determined using selected global clotting tests.

It was also surprising to find that the "FVII activator" is likewise able to bring about effective activation of single chain urokinase (scuPA, single chain urokinase plasminogen activator) and single chain tPA (sctPA, single chain tissue plasminogen activator), that is can act as a plasminogen activator activator (PAA). The activity of the activated PAs can be measured, for example, using chromogenic substrates. Accordingly, this property can therefore also be used for detecting and quantifying the "FVII activator." The activation of the plasminogen activators can also be determined in a coupled reaction in the presence of plasminogen, either by the formation of plasmin itself or by the dissolution of a fibrin clot which is brought about by plasmin.

In summary, therefore, it can be stated that the protease can be both detected and quantified by incubating it with a solution containing FVIII or FVIIIa and then determining the remaining quantity of FVIII/VIIIa by means of a suitable activity test. In the same way, FV or FVa can be incubated with the protease and the remaining quantity of FV/FVa can subsequently be quantified. The unknown protease concentration can be determined quantitatively by comparison with a standard curve of increasing quantities of protease which is included in the test. Various global clotting tests are likewise suitable for the quantification, with the protease concentration being read off a calibration curve on the basis of the shortening of the clotting time. The PAA activity of the protease can also be used for determination purposes.

Another feature of these tests is that the FV and FVIII inactivation and the PAA activity are displayed particularly well in the presence of adequately high concentrations of calcium, preferably >0.001 mM, particularly preferably >0.005 mM, e.g. in the form of $CaCl_2$. In contrast to the direct chromogenic assay, in which, as has been described above, both heparin and heparin-like substances and also calcium increase the protease activity, the inactivation of FV/FVIII is not promoted, or only promoted insignificantly, by heparin. By contrast, the PAA activity is stimulated in the presence of both agents, that is by calcium and/or heparin or heparin-like substances.

The protease-mediated reactions can be very efficiently diminished or prevented by incubating the protease with inhibitors, particularly antithrombin III in the presence of heparin or heparin-like substances (preferably in the presence of heparin), C1-esterase inhibitor, alpha2-antiplasmin, inter-alpha-trypsin inhibitor or known synthetic, low molecular weight protease inhibitors such as Guanidinocaproic acid-para-ethoxycarbonylphenylester, which is available under the trademark FOY®. These substances can therefore be used for stopping the reaction, in order, for example, to define incubation times precisely or to increase the specificity of the test still further. Decreasing the free calcium ions in the mixture with a chelating agent, for example, can also be used for this purpose.

2. STABILIZED PREPARATIONS OF FACTOR V AND FACTOR VIII

The further task now ensued, from the above-described observations concerning the proteolytic actions of the novel protease on clotting factors V and VIII, of inhibiting the protease or reducing its activity in order to avoid losses of yield and the formation of what might possibly be interfering protein fragments. This is all the more relevant since FV and FVIII are usually prepared from cryoprecipitates which have been obtained from plasma and in the presence of calcium ions because the latter are required for maintaining protein conformations.

Another part of the subject matter of the invention is therefore a stabilized preparation of FV or FVIII which is free of the factor V or factor VIII fragments formed due to proteolytic degradation as a result of the fact that the protease activating the blood clotting factor VII is inhibited. Since more detailed investigations have shown that inactivation of factor V and factor VIII by said protease takes place particularly efficiently in the presence of calcium ion concentrations greater than 0.5 mM, the factor V or VIII preparation can be effectively stabilized if, for the inhibition of the protease activating the blood clotting factor VII, the concentrations of calcium ions in the factor V or in the factor VIII preparation are adjusted to less than 1.0 mM, preferably to less than 0.5 mM. While the factor V- and factor VIII-inactivating properties of the protease are markedly reduced at these concentrations, the quantity of calcium ions is still sufficient for stabilizing the conformations of the FV and FVIII molecules. The abovementioned quantities of calcium ions should not be exceeded, not merely in the end product but also in the cryoprecipitate itself and in the following purification steps.

In accordance with the above-described affinity of the protease or the proenzyme for heparin and heparin-like substances, the protease/proenzyme can be removed from the FVIII- or FV-containing solution by incubating with immobilized herapin or other suitable immune- or affinity-adsorbents. Polyclonal or monoclonal antibodies, and respective antibody fragments that are useful in preparing the immune adsorbents are readily available by techniques known in the art in using all or part of the protease or proenzyme as antigen.

However, natural or synthetic protease inhibitors can also be employed, where appropriate in addition to decreasing the quantity of calcium ions, for preventing the proteolytic degradation of the FV or the FVIII. Proteins such as aprotinin, alpha2-anbplasmin, C1-esterase inhibitor or inter-trypsin inhibitor may be employed as inhibitors. Low molecular weight substances which are known to the skilled person as synthetic serine protease inhibitors can also be used in this context. Inhibitors, such as antithrombin III, whose inhibitory potential is increased by heparin or heparinoids can likewise be added. Thus, it has been found, surprisingly, that while heparin on its own is able to increase the amidolytic activity of the protease towards small chromogenic substances, it does not support inactivation of FV/FVIII.

3. PHARMACEUTICALS WHICH COMPRISE THE NOVEL PROTEASE

The novel protease and/or its proenzyme can also be used therapeutically.

They can be employed as a blood coagulating agent, either on their own or together with substances which increase the activity of the protease, such as heparin, or heparin-related substances, such as heparan sulfate, and/or calcium ions, with it being possible additionally to add factor VII as well, in its inactive form, to this agent. The use of such an agent, in which its FVIII-bypassing activity (FEIBA) is exploited, for example, can be indicated when intolerances exist toward FVIII and/or FIX and/or FXI and/or the contact phase proteins, such as FXII, for example on account of the presence of antibodies, or when other types of deficiency situations exist. In this connection, the FVII can be activated either in vitro, in the plasma, in enriched fractions or by acting on purified FVII. It is also possible to use the novel blood coagulating agent ex vivo for general hemorrhage prophylaxis or for staunching hemorrhages.

The present invention also relates to use of the protease or its proenzyme, optionally together with proenzyme activators prepared from blood plasma or prothrombin complex (PPSB) concentrates or expressed recombinantly or transgenically for the promotion of wound healing and hemostasis, as an additive of a fibrin adhesive or fleece or other release system which is suitable for rapid wound closure, based on fibrin, for substitution in inborn or acquired deficiency states of this protease or its proenzyme, in the presence of antibodies against the blood clotting factor VIII or for the in vitro activation of factor VII.

On the other hand, the observed inhibition of the novel protease by aprotinin or the abovementioned inhibitors can be used for developing an agent which comprises a protease inhibitor and which diminishes the ability of the blood to coagulate. In addition to this, the novel protease can also be used to identify physiological or non-physiological factors, such as synthetic peptides, which impair blood clotting because of their protease-inhibiting effect. The peptide sequences of the chromogenic substrates which are transformed particularly efficiently, such as those of the S 2288 (see above for details), can be used as a structural basis for this. The addition of suitable inhibitors to clotting preparations, or during their preparation, can be necessary if these preparations are to be free of proteolytic activities.

Surprisingly, a property has now been found, in association with characterizing the protease further, which opens up the possibility of an additional use for the so-called "factor VII activator" protease. When single chain plasminogen activators such as prourokinase (single chain urokinase, scuPA, single chain urokinase plasminogen activator) or sctPA (single chain tissue plasminogen activator) are incubated, the "factor VII activator" brings about activation of these plasminogen activators (PA). In this connection, there is a limited proteolysis of the single chain PAs, resulting in the formation of double chain proteases, which are particularly suitable for activating plasminogen. The resulting plasmin is the effector of fibrinolysis, that is the physiological system which is responsible for dissolving thrombi. PAs, such as prourokinase or tPA, are endogenous proteins which are released when needed and which, as is known, are activated by plasmin or by kallikrein (scuPA). The mechanism by which scuPA is activated in the healthy state has not yet been fully clarified.

The plasminogen activators are employed therapeutically, as isolated or recombinantly prepared proteins, in pharmaceutical preparations in association with thromboembolic diseases or complications, such as in leg vein thrombosis, cardiac infarction or strokes.

In accordance with the properties of the "factor VII activator" which have now been found, the latter can be used for in vivo or ex vivo activation of plasminogen activators such as prourokinase or sctPA. This activity can also be applied by using said protease for the prophylaxis or therapy of thromboembolic diseases, specifically in combination with single chain or double chain plasminogen activators or anticoagulants as well. This possible use is not contradictory to the fact that the protease is also able to act in a procoagulatory manner. The question of which of the two reactions predominates is probably resolved by the availability of the physiological substrates. According to the current state of knowledge, factor VII is activated moderately in plasma and continuously maintains a certain concentration of FVIIa in order to be able to counteract immediately any sudden vascular damage. On the other hand, only nanogram quantities of tissue plasminogen activator and urokinase plasminogen activator are present in a milliliter of blood plasma. It is only when fibrin deposition or thrombi occur that there is an increase in the concentration, by secretion or synthesis, of plasminogen activators, which then display their thrombolytic activity by activating plasminogen after they have been activated locally, in particular when bound to the thrombus. When single-chain PAs are present, particularly in a locally restricted manner, their activation might outweigh FVII activation, thereby making it possible to adjust to the physiological situation. Accordingly, this protease might also regulate hemostasis, thereby indicating a replacement with the protease and/or the proenzyme in the case of inborn and acquired deficiency states.

Another part of the subject matter of the invention is therefore a pharmaceutical preparation which comprises a quantity of the blood clotting factor VII-activating protease and/or its proenzyme form which is sufficient for dissolving fibrin-containing thrombi. This preparation may additionally comprise single chain plasminogen activators (PA) and/or anticoagulants. When the proenzyme is present it is advantageous to comprise a suitable activating agent within or together with the pharmaceutical preparation above.

Since it has been found that the plasminogen activator-reinforcing effect of the "FVII activator" is particularly promoted by calcium and/or heparin and heparin-like substances such as dextran sulfate, pharmaceutical preparations which additionally comprise soluble calcium salts and/or heparin or heparin-like substances may particularly advantageously be employed for dissolving, in accordance with the invention, fibrin-containing thrombi. In this context, the protease/proenzyme can be employed on its own or in combination with single chain or double chain plasminogen activators with or without substances which exhibit particular affinities for the protease and thereby increase its activity as carrier substances for prolonging plasma half life or as mediators to surfaces.

Pharmaceutical preparations which comprise the blood clotting factor VII-activating protease can, because of its special fibrinolytic effect, be employed for treating diseases which are caused by fibrin-containing thrombi. Fibrinolytic processes are also involved in wound healing processes. In this connection, said protease and/or proenzyme can be administered intravenously or locally, subcutaneously, intradermally or intramuscularly, or else topically in the case of injuries and wounds, or bound to a suitable carrier matrix. Both protease/proenzyme which has been isolated from body fluids such as blood or plasma and protease/proenzyme which has been prepared recombinantly or transgenically can be employed in this context. The protease/proenzyme is also suitable for use as a component of a so-called fibrin adhesive, which should not then contain any substance, such as aprotinin, which inhibits the protease/proenzyme. In this case, use can be made of the clotting-shortening properties of the protease.

The protease/proenzyme above may be used for inherited or acquired hemostasis deficiencies, in (diffuse) bleeding occurrences respective thrombosis associated complications. If used to treat bleeding the combination of protease/proenzyme together with FVIII optionally under addition of further clotting factors is advantageous.

4. PROCESS FOR PASTEURIZING THE FVII-ACTIVATING PROTEASE

As a protein which has been isolated from human plasma, the novel protease and/or its proenzyme can only be employed as a pharmaceutical preparation if it has previously been subjected to a process for inactivating viruses. The pasteurization process is in particular recognized as being the most important process for inactivating viruses. However, heating at about 60° C. for up to 10 hours requires the protein which is to be treated to be of adequate stability. The optimal stabilizers have to be determined separately for each protein and their concentrations have to be optimized.

In the case of the novel protease and/or its proenzyme, conditions which stabilize the protein in solution, without any pasteurization being performed, have already been mentioned above. In this regard, a slightly acidic pH range has in particular proved to be advantageous. However, when a pasteurization is carried out under these conditions, the novel protease and/or its proenzyme as a rule loses more than 50% of its original activity.

It has now been found that a pasteurization of a pharmaceutical preparation comprising the novel protease and/or its proenzyme ensures optimal stabilization results if the preparation is prepared a) in a pH range of from 3.5 to 8.0, preferably in a pH range of from 4.0 to 6.8;
b) in the added presence of one or more amino acids in a quantity of more than 0.01 mol/l, preferably more than 0.05 mol/l; and/or
c) in the added presence of a sugar or of a combination of different sugars having a total concentration of more than 0.05 g/ml, preferably more than 0.2 g/ml; and/or
d) in the added presence of one or more substances which are able to complex calcium ions, such as citrate, oxalate, ethylenediamine tetraacetic acid, etc.

Additives such as albumin, Haemaccel®, heparin and heparinoids, glycerol, glycol and polyethylene glycol, may also be used separately or mixed together. After the pasteurization has been completed, the sugars, amino acids and other additives which have been added as stabilizers can be decreased, or removed completely from the preparation, using methods with which the skilled person is familiar. The results of the pasteurization processes are given in Examples 12 and 13.

EXAMPLE 1

The Staclot® FVIIa-rTF test system (Stago/Boehringer Mannheim) was used for demonstrating activation of FVII by the prepared protease. This detection system is based on the particular property of (recombinant) soluble tissue factor (rTF) which is only able to use the preformed activated FVII (FVIIa) for initiating the extrinsic clotting pathway. In contrast to the situation when complete tissue factor is used, this makes it possible to determine the real content of FVIIa precisely.

Isolated FVII (Enzyme Research Labs) was used for the activation experiments. This FVII itself contains traces of FVIIa since it is isolated from human plasma. The concentration was adjusted to 0.05 IU of FVII/ml by diluting with buffer. The FVII was incubated at room temperature for 10 min with the test substances and then tested for the true FVIIa content. The FVIIa contents were quantified using a reference curve which was constructed in parallel.

It was ascertained in preliminary experiments, which are not described here, that while, in the concentration employed, aprotinin completely inhibited the activity of the prepared protease, it had no direct effect on the FVIIa nor any significant effect on the FVIIa-rTF test system.

The results given below relate in each case to triplicate determinations.

The following experimental assays were accordingly set up:

1. FVII:
Result: 10 mIU of FVIIa/ml
Non-activated FVII was used as the control assay. This already contains traces of FVIIa (see above) in the order of magnitude of 10 mIU of FVIIa/ml.

2. FVII+Aprotinin:
In this assay, FVII was incubated in the presence of aprotinin and used in the FVIIa-rTF assay in order to demonstrate that FVIIa itself was not inhibited, and nor was the test affected by the aprotinin employed. This was confirmed (in comparison with assay 1).

3. Protease+FVII (Incubation), Followed by the Addition of Aprotinin:
Result: 18 mIU of FVIIa/ml
In this case, the protease was given time to activate FVIIa. Aprotinin was only added, in order to inhibit the protease, after the 10-minute incubation had taken place. The resulting FVIIa was quantified in the FVIIa-rTF assay. Subtracting the FVIIa base value (assay 1), 8 mIU of FVIIa/ml have therefore been formed by the action of the protease under the chosen conditions.

4. Protease+Aprotinin, Followed by the Addition of FVII
Result: 11 mIU of FVIIa/ml
In this assay, the protease was inhibited with aprotinin before contact with FVII. Neither the subsequent incubation with FVII, nor the following FVIIa quantification led to any significant increase in the FVIIa content (because of the range of variation in the assay, 11 versus 10 mIU/ml in assay 1 is not to be regarded as being significant).

5. Protease
Result: 0 mIU of FVIIa/ml
This assay demonstrated that, at the concentration selected, the protease did not itself have any effect on the FVIIa-rTF test system.

In summary, it follows from the above that
the described protease activates FVII;
the activation of FVII by the protease takes place "directly," that is independently of the presence of rTF;
the activation of FVII can be inhibited by aprotinin; at the concentration selected, aprotinin itself does not have any significant influence on the test system.

EXAMPLE 2

This example describes how FVII is activated in a reaction which is dependent on the concentration of the protease and on the time over which the protease is incubated with FVII.

Test systems and reagents were selected to correspond with the conditions described in Example 1. In a first series of experiments, the initially introduced FVII was preincubated with different dilutions (1:5, 1:10 and 1:20) of the protease-containing solutions (5 min at RT), then treated with aprotinin (to inhibit the protease) and subsequently tested for its content of FVIIa in the FVIIa-rTF assay.

Once again, the parallel assays, in which the protease had been inhibited by aprotinin before contact with FVII, served as control assays.

The results are given as activation factors, i.e. correspond to x times the value which was measured in the abovementioned control assay.

| Assay | Control |
| --- | --- |
| Protease + FVII Incubation + Aprotinin | Protease + aprotinin Incubation + FVII |

| Dilution of the protease solution | Activation factor | |
| --- | --- | --- |
| 1:5 | 2.6 | 1.0 |
| 1:10 | 2.0 | 1.0 |
| 1:20 | 1.6 | 1.0 |

The activation factor 1:0 of the control assays corresponds to the control, which was additionally included and in which only the test buffer, containing the FVII employed, was treated under identical incubation conditions and tested. That is, no significant activation took place in the control assays.

It follows from this that FVII is activated by the protease in a manner which is dependent on the concentration of the protease. It was similarly demonstrated that, when the concentrations of the coreactants are kept constant, the FVII is activated by the protease in a manner which is dependent on the length of the incubation.

When equal volumes of a solution containing 0.2 IU of FVII/ml and a 1:10-diluted protease solution were incubated together, the following contents of FVIIa were obtained after incubating for the relevant times and subsequently adding aprotinin (in order to stop the activation):

| Length of incubation | Activation factor |
| --- | --- |
| 0 min | 1.0 |
| 2.5 min | 1.3 |
| 5.0 min | 2.0 |
| 10.0 min | 2.8 |
| 40.0 min | <3.8 |

It follows from this that FVII is activated by the protease in a time-dependent manner.

EXAMPLE 3

Using this example, it will be demonstrated that activation of FVII by the protease is increased in the presence of calcium ions and heparin.

25 µl of the protease-containing solution were mixed with 50 µl of
buffer (control)
15 mM $CaCl_2$
50 USP units of heparin/ml
Pathromtin (lipid mixture, aliquot dissolved in accordance with the manufacturer's instructions)
at room temperature for 5 min, and then treated with 150 µl of a tris/NaCl buffer solution (pH 8.2) and 25 µl of the chromogenic substrate S2288 (3 mM); the time-dependent change in the extinction at 405 nm was then measured (at 37° C.). The activation factors, related to the buffer control (x times), are given in the following table.

| Assays | Activation factor (x times buffer control) |
| --- | --- |
| Buffer control | 1.0 |
| +$CaCl_2$ | 3.6 |
| +Heparin | 2.6 |
| +Lipid | 0.9 |
| +$CaCl_2$ + heparin | 4.3 |
| +$CaCl_2$ + lipid | 3.3 |
| +Heparin + lipid | 2.7 |
| +$CaCl_2$ + heparin + lipid | 3.7 |

Under the conditions used in this example, marked increases in the activity of the protease can be observed in the presence of calcium ions and/or heparin.

EXAMPLE 4

In each case, 25 µl of a solution, containing 10, 1 or 0.1 µg of protease/ml, were mixed with 25 µl of FVIII (2 IU/ml), after which 25 µl of CaCl₂ (25 mM) and 25 µl of Pathromtin® (Dade Behring GmbH) were added. After incubating at 37° C. for 0, 3, 10 and 20 min, the reaction was stopped by adding 400 µl of aprotinin (500 KIU/mg). A sample in which aprotinin was introduced initially served as a control.

Each sample was diluted in tris-buffer/BSA. In each case, 50 µl of this solution were mixed with 50 µl of the factor reagent (essentially composed of FIXa, FX and a thrombin inhibitor, appropriately modified in accordance with the Coamatic® FVIII test, Chromogenix AB) and incubated at 37° C. for 10 min. After 50 µl of substrate (e.g. S 2765, N-a-Cbo-D-Arg-Gly-Arg-pNA) had been added, the reaction was stopped after a predetermined period of incubation by adding 50 µl of acetic acid (50%), and the OD405 nm was then measured. A standard curve for FVIII was used for determining the concentration in the sample.

Figure 1:
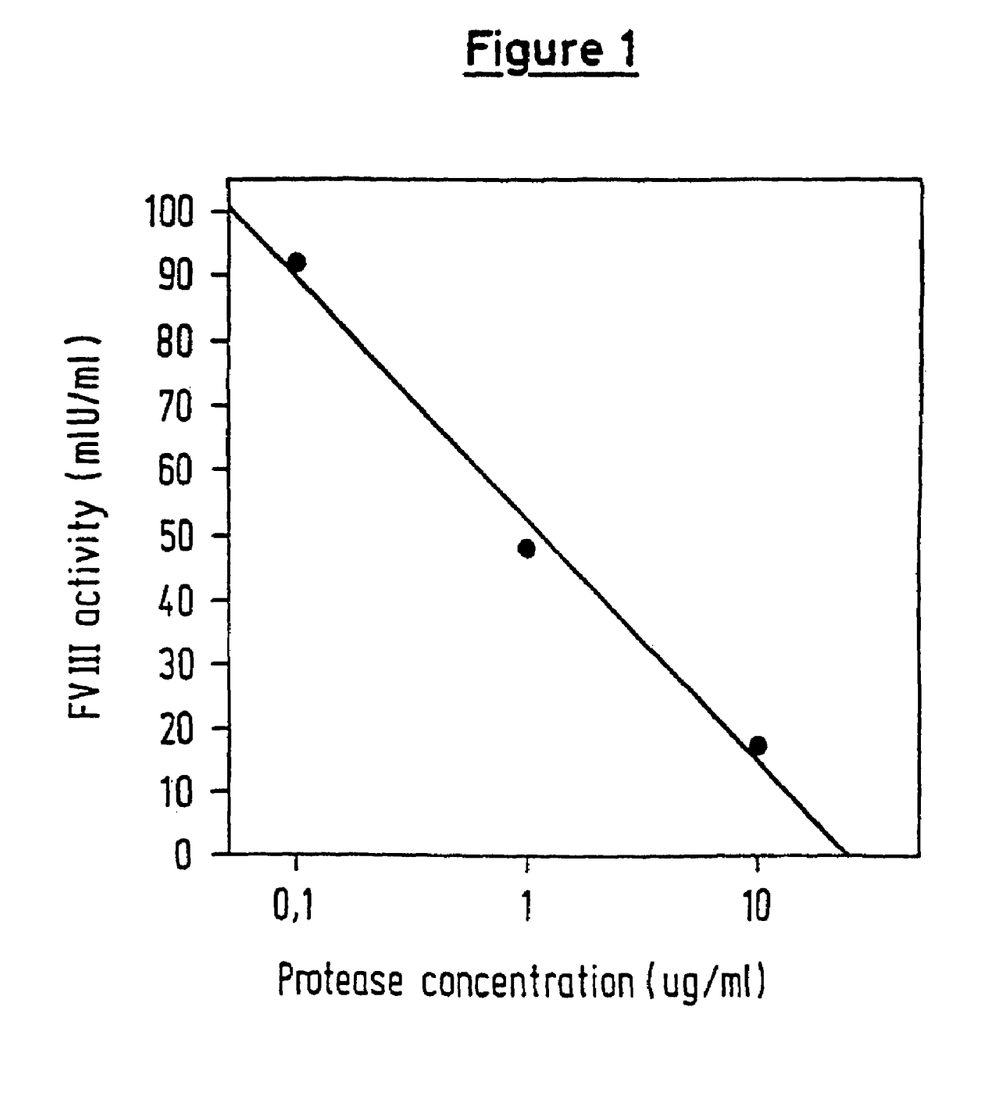
FIG. 1 depicts the level of FVII activity as the protease concentration is increased while the incubation time remains constant.

Results:

In a first assay, the time for which the protease was incubated with FVIII (2 IU/ml) was kept constant (10 min) but the concentration of the protease was varied (0.1, 1 and 10 µg/ml). The reaction was stopped and the residual concentration of active FVIII was determined. As the protease concentration increased, correspondingly more FVIII was inactivated (FIG. 1).

The protease content of a sample can be quantified using an appropriate standard curve.

Figure 2:
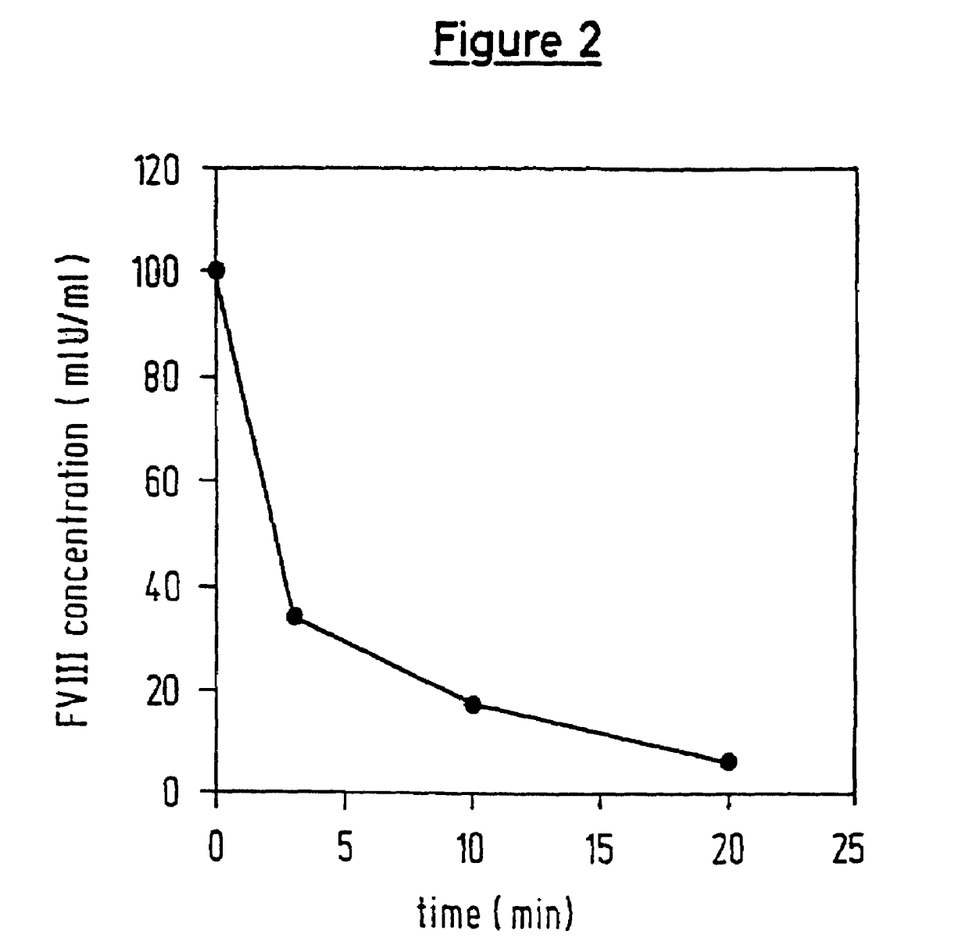
FIG. 2 depicts the level of FVII concentration as the incubation time is increased while the protease concentration remains constant.

In a second assay, the concentration of the protease was kept constant (10 µg/ml) but the time of incubation with FVIII (2 IU/ml) was varied. A marked reduction in the residual concentration of active FVIII was seen as the length of incubation increased (FIG. 2).

EXAMPLE 5

The influence of the "FVII activator" on the activity of the factor V was investigated:

25 µl of protease-containing solution (0-100 µg/ml) were incubated with 50 µl of FV (5 IU/ml) and 25 µl of 25 mM CaCl₂ (0-20 min) and, after that, 400 µl of buffer containing 100 KIU of aprotinin/ml were added.

In each case, 100 µl of each incubation assay were then incubated with 100 µl of FV-deficient plasma at 37° C. for 1 min, after which 200 µl of Thromborel S® were mixed in and the clotting times were determined in a Schnitger and Gross coagulometer. The residual activities of FV were determined.

Results:

| Protease concentration | Residual FV activity Time for which protease incubated with FV (min) | | |
|---|---|---|---|
| (µg/ml) | 0 | 0 | 20 |
| 10 | 93 | 91 | 100 |
| 30 | 100 | 93 | 28 |
| 100 | 100 | 29 | 13 |

This example demonstrates that FV was inactivated by the protease over time.

EXAMPLE 6

The influence of the "FVII activator" on clotting times in so-called global test was investigated using Schnitger and Gross coagulometers. All the difference values listed correspond to the clotting times which were shortened by this amount.

NAPTT (Non-Activated Partial Thromboplastin Time)

The protease-containing solution was diluted with buffer down to 100, 30, 10 and 3 µg/ml. 100 µl of each of these solutions were incubated, at 37° C. for 2 min, with 100 µl of citrate plasma (standard human plasma pool or individual donors) and 100 µl of Pathromtin®, after which 100 µl of 25 mM CaCl₂ were added; the clotting times were then determined. The differences between these measured values and the corresponding clotting times obtained with buffer solution instead of the protease were determined.

| | Clotting time differences (buffer minus sample) (sec) Protease concentration (µg/ml) | | | |
|---|---|---|---|---|
| Sample No. | 3 | 10 | 30 | 100 |
| Standard human plasma (213 sec) | 13 | 20 | 42 | 43 |
| 1 | 20 | 33 | 42 | 41 |
| 2 | 27 | 31 | 45 | 47 |
| 3 | 13 | 14 | 23 | 29 |
| 4 | 18 | 37 | 51 | 50 |
| 5 | 25 | 49 | 54 | 46 |

The addition of FVII-activator resulted in a concentration dependent shortening of NAPTT.

Plasma Recalcification Time

The protease-containing solution was diluted with buffer down to 100, 30, 10 and 3 µg/ml. 100 µl of each of these solutions were incubated with 100 µl of citrate plasma (standard human plasma pool or individual donors) at 37° C. for 1 min, after which 100 µl of 25 mM CaCl₂ were added; the clotting times were then determined. The differences between these measured values and the corresponding clotting times obtained with buffer solution instead of protease were determined.

| | Clotting time differences (buffer minus sample) (sec) Protease concentration (µg/ml) | | | | |
|---|---|---|---|---|---|
| Sample No. | 0 | 3 | 10 | 30 | 100 |
| Standard human plasma (283 sec) | 0 | 17.2 | 15.1 | 30.5 | 50.4 |
| 1 | 0 | 29.8 | 51.7 | 60.3 | 90.1 |
| 2 | 0 | 25.2 | 51.7 | 69.5 | 101.3 |
| 3 | 0 | 28.0 | — | 39.0 | 74.6 |
| 4 | 0 | 27.3 | 42.7 | 55.6 | 91.8 |
| 5 | 0 | 44.3 | 69.1 | 101.2 | 134.2 |

PT (Prothombin Time)

The protease-containing solution was diluted with buffer down to 100, 30, 10 and 3 µg/mL. 100 µl of each of these solutions were incubated with 100 µl of citrate plasma (standard human plasma pool or individual donors) at 37° C. for 1 min, after which 200 µl of Thromborel S® (Dade Behring GmbH) were added; the clotting times were then determined.

The differences between these measured values and the corresponding clotting times obtained with buffer solution instead of protease were determined.

|  | Clotting time differences (buffer minus sample) (sec) Protease concentration (µg/ml) | | | | |
|---|---|---|---|---|---|
| Sample No. | 0 | 3 | 10 | 30 | 100 |
| Standard human plasma (283 sec) | 0 | 1.0 | 1.7 | 1.5 | 2.4 |
| 1 | 0 | 0.7 | 1.3 | 2.4 | 2.7 |
| 2 | 0 | 0.3 | 0.4 | 1.7 | 3.1 |
| 3 | 0 | 0.4 | 0.7 | 1.5 | 1.8 |
| 4 | 0 | 0.1 | 0.7 | 1.8 | 3.1 |
| 5 | 0 | 0.3 | 0.5 | 1.2 | 2.8 |

The clotting times in the above global tests were shortened in a manner which was dependent on the concentration of the protease. In a corresponding manner, it was possible, after "calibrating" a plasma which was used with a known quantity of the "FVII activator," to determine the protease concentration in a sample by reading off from a standard curve.

EXAMPLE 7

The plasminogen activator-activating properties of the "FVII activator" were investigated using single chain urokinase (scuPA) and single chain tPA (sctPA).

Assay:

| | |
|---|---|
| 0.1 ml of | PA solution (20 µg of scuPA/ml or 100 µg of sctPA/ml) |
| +0.1 ml of | test buffer of |
| | 100 U of heparin/ml in test buffer or |
| | 20 mM CaCl$_2$ in the test buffer |
| +0.5 ml of | test buffer |
| +0.1 ml of | protease/sample (increasing concentrations: |
| | 2-10 µg of scuPA/ml or |
| | 50-200 µg of sctPA/ml) |
| Incubation at 37° C. | |
| +0.1 ml of | 100 KIU of aprotinin/ml in test buffer |
| Incubation at 37° C. for 2 min | |
| +0.1 ml of | substrate S-2444 (3 mM) |

As a control, aprotinin was introduced initially, instead of the plasminogen activator (PA), prior to the first incubation, and carried through in each case. In return, PA was not added until later, in place of the aprotinin.

The difference between the measurements ($\Delta$) $\Delta OD_{405nm}$ was determined photometrically. The control values which were obtained were subtracted from the sample/protease values and in this way the PA activity which was caused by the PAA activity was determined (in mIU/min).

Results:

scuPA Activation (20 µg of scupPA/ml, 2-10 µg of "FVII Activator"/ml)

| A. Stimulant: none | | | |
|---|---|---|---|
| Incubation time | Resulting PA activity ($\Delta$ mIU/min) "FVII activator" (µg/ml) | | |
| (min) | 2 | 5 | 10 |
| 2 | 25 | 60 | 117 |
| 5 | 79 | 179 | 165 |
| 10 | 186 | 449 | 517 |

| B. Stimulant: heparin | | | |
|---|---|---|---|
| Incubation time | Resulting PA activity ($\Delta$ mIU/min) "FVII activator" (µg/ml) | | |
| (min) | 2 | 5 | 10 |
| 2 | 190 | 332 | 425 |
| 5 | 330 | 455 | 458 |
| 10 | 417 | 462 | 460 |

| C. Stimulant: CaCl$_2$ | | | |
|---|---|---|---|
| Incubation time | Resulting PA activity ($\Delta$ mIU/min) "FVII activator" (µg/ml) | | |
| (min) | 2 | 5 | 10 |
| 2 | 255 | 370 | 401 |
| 5 | 338 | 424 | 438 |
| 10 | 416 | 445 | 448 |

The tables illustrate the fact that scuPA was activated in a manner which was dependent on the concentration of the "FVII activator" and on the length of the incubation. At the same time, both heparin and calcium had a stimulatory effect on the activation of the PA which was brought about by the protease.

sctPA Activation (100 µg of sctPA/ml, 50-200 µg of "FVII Activator"/ml

Since the turnover rate of the activated tPA only increases by a factor of 3-4 as compared with the tPA proenzyme (while that of uPA increases by a factor of 1000-1500), higher concentrations of the two coreactants (see above) had to be selected in order to obtain an analyzable measurement signal.

| Incubation time (min) | Resulting PA activity ($\Delta$ mIU/min) "FVII activator" (µg/ml) |
|---|---|
| 1 | 10.2 |
| 2 | 16.8 |
| 5 | 38.8 |
| 10 | 60.2 |
| 20 | 73.3 |

B. Dependence on the Concentration of the "FVII Activator" (Incubation Time: 20 min, at 37° C.), Stimulant: Heparin (100 IU/ml)

| "FVII activator" (µg/ml) | PA activity ($\Delta$ mIU/min) |
|---|---|
| 50 | 33.6 |
| 100 | 51.0 |
| 200 | 71.9 |

C. Stimulants (Period of Incubation: 20 min, at 37° C.)

| Stimulant | PA activity (Δ mIU/min) |
|---|---|
| None | 5.9 |
| CaCl$_2$ | 25.3 |
| Heparin | 63.8 |

The tables demonstrate that sctPA was also activated in a manner which was dependent on the concentration of the protease and on the incubation time. Both heparin and calcium ions had a stimulatory effect on the PA-activating ability of the "FVII activator."

EXAMPLE 8

Two FVIII-containing solutions, one of which was essentially free of von Willebrand Factor while the other contained vWF, were incubated with the abovementioned protease in the presence of calcium. After predetermined times, the residual FVIII activities were determined by means of a chromogenic test and related to the control assays without protease.

For this, 25 μl of a solution containing 0.1 IU of FVIII/ml were treated with the same volume of the protease solution (10 μg/ml) and the whole was mixed with 25 μl of CaCl$_2$ (25 mM). After incubation periods of 0, 5, 10 and 20 min at 37° C., the assays were in each case treated with 400 μl of a solution containing 200 KIU of aprotinin/ml in order to stop the proteolytic activity of the protease. Preliminary experiments had shown that this concentration of aprotinin had no significant interfering effect on the FVIII activity test described below (assays 1+3). In assay 2, the protease was incubated with aprotinin prior to contact with FVIII, after which the procedure was as described above.

In each case, 50 μl of the stopped sample (or after further dilution) were then treated with the so-called factor reagent, essentially composed of FIXa, FX and a thrombin inhibitor, and incubated at 37° C. for 10 min. Following the addition of 50 μl of a chromogenic substrate which is cleaved by activated FX, the reaction was stopped after 5 minutes of incubation by adding 50 μl of acetic acid (50%); the $\Delta OD_{405nm}$ was then measured. The FVIII activity (mIU) was ascertained with the aid of a standard curve which was constructed using a dilution series which was prepared from the FVIII concentrate and which was included in the test.

The FVIII activities are given in percentages of the controls to which protease was not added.

Results:

| | FVIII activity (%) Incubation period (min) | | | |
|---|---|---|---|---|
| Assay | 0 | 5 | 10 | 20 |
| 1. FVIII | 97 | 27 | 11 | <1 |
| 2. FVIII/aprotinin | 98 | 97 | 97 | 96 |
| 3. FVIII/vWF | 98 | 16 | 14 | 1 |

In the presence of CaCl$_2$ (in this case 6.25 mM), FVIII was inactivated by the protease in a manner which was dependent on the length of the incubation. The vWF did not protect the FVIII from inactivation by the protease. Inhibition of the protease with aprotinin prior to contact with FVIII prevented the latter from being inactivated.

EXAMPLE 9

This experimental series was carried out as described in example 1/assay 1, but in this case the concentrations of calcium in the mixtures of protease and FVII were varied. For this, CaCl$_2$ was added, from the stock solution of calcium, up to the final concentrations shown in FIG. 3.

Results:

If the concentration of calcium in the assay is decreased below 1 mM, approx. 50% of the FVIII is then spared under these conditions. Below 0.5 mM calcium, the percentage spared is more than 60% (FIG. 1).

Figure 3:
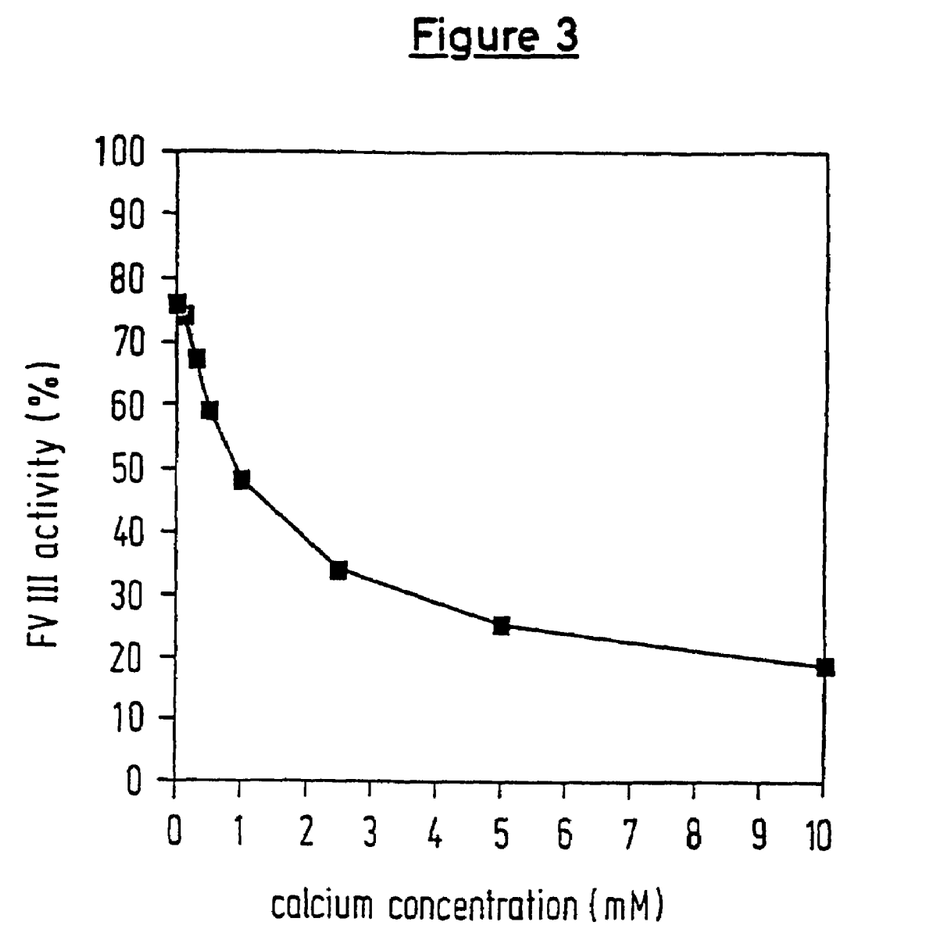
FIG. 3 depicts the level of FVII activity as the concentration of calcium is increased.

If the concentration of calcium in the assay is decreased below 1 mM, approx. 50% of the FVIII is then spared under these conditions. Below 0.5 mM calcium, the percentage spared is more than 60% (FIG. 3).

EXAMPLE 10

The influence of the "FVII activator" on the clotting times in so-called global test was investigated by means of thromboelastography.

The change in the shear elasticity or the strength of the relevant blood clot was recorded continuously using a Hilgard TEG meter (from Hellige). The so-called r and k values are, respectively, the times from the beginning of blood withdrawal and from the start of the clotting reaction, and, in the case of citrate blood plasma, the time of recalcification until the TEG curve has been broadened by 1 mm and the time from the endpoint of the r value until the curve has been broadened to 20 mm (clot formation time).

For this, aliquots of 150 μl of blood or plasma from 5 donors were in each case incubated in the measuring cuvettes at 37° C. for 2 min, after which 50 μl of sample (protease) were mixed in. The reaction was started by adding 100 μl of 25 MM CaCl$_2$. The final concentration of the "FVII activator" in the assay was 15 μg/ml. The shortening of the r time was measured in relation to the assay which contained buffer instead of the sample.

Results:

| Blood No. | Sample | r time (min) | k time (min) | r + k time (min) |
|---|---|---|---|---|
| 1 | Protease | 5.2 | 3.4 | 8.6 |
| 1 | Buffer | 7.8 | 5.6 | 13.4 |
| 2 | Protease | 5.2 | 5.1 | 10.3 |
| 2 | Buffer | 6.8 | 7.1 | 13.9 |
| 3 | Protease | 4.0 | 5.2 | 9.2 |
| 3 | Buffer | 6.5 | 6.3 | 12.8 |
| 4 | Protease | 4.5 | 4.8 | 9.3 |
| 4 | Buffer | 4.8 | 6.0 | 10.8 |
| 5 | Protease | 4.2 | 3.8 | 8.0 |
| 5 | Buffer | 7.0 | 5.8 | 12.8 |

| Plasma No. | Sample | r time (min) |
|---|---|---|
| 1 | Protease | 9.0 |
| 1 | Buffer | 11.3 |
| 2 | Protease | 9.2 |
| 2 | Buffer | 12.5 |
| 3 | Protease | 9.5 |
| 3 | Buffer | 9.6 |
| 4 | Protease | 8.2 |
| 4 | Buffer | 12.1 |

| Plasma No. | Sample | r time (min) |
|---|---|---|
| 5 | Protease | 9.7 |
| 5 | Buffer | 14.1 |

This example makes clear that, in almost all cases, addition of the protease resulted in a marked shortening of the clotting time. In this present instance, the fibrinolytic properties of the "FVII activator" receded into the background. A reason for this is that in "normal subjects," the concentrations of plasminogen activator in the plasma lie in the nanogram region and do not have any effect in the in-vitro clotting test.

EXAMPLE 11

The FVIII-bypassing activity of the protease was demonstrated by the following experimental assay: thromboelastography was used as the measuring technique. The r time was evaluated (see Example 10). A sample of whole blood was incubated with a monoclonal antibody, whose FVIII-activity-inhibiting properties were known, in order to simulate the presence of a naturally occurring FVIII inhibitor (antibody against FVIII). This sample was compared with the whole blood sample control (buffer instead of Mab). The FEIB activity of the protease was tested by adding the protease (final concentration 17 μg/ml) to the whole blood sample which had been inhibited by the Mab. Protease was added to a further sample, and the effect of the protease, on its own, on the r time was determined.

Results:

|  | r time |
|---|---|
| Whole blood control | 8.0 |
| Whole blood + mAb | 11.0 |
| Whole blood + mAb + protease | 8.0 |
| Whole blood + protease | 3.5 |

The lengthening of the r time, caused by the anti-FVIII rnAb, was normalized once again by the presence of the protease, thereby illustrating the FEIB activity of the protease. On its own, the protease shortened the clotting time, as already demonstrated above.

EXAMPLE 12

The following substances were added to a solution, which contained 50 μg of the FVII-activating protease/ml, to give the corresponding final concentrations:

25 mM Na citrate
25 mM HEPES
100 mM arginine
0.75 g of sucrose/ml

The solution was divided into portions and the aliquots were in each case adjusted to different pH values of from 5.0 to 8.6 and then heated at 60° C. for 10 hours.

The activities of the heated protease solutions were determined in a chromogenic test, with the time-dependent amidolysis of the chromogenic substrate S2288 (H-D-Ile-Pro-Arg-pHA×2 HCl, Chromogenix AB, Sweden) being recorded. This activity was expressed as a percentage of the aliquots which were unheated and were measured in parallel:

Results:

| Assay | Activity (%) |
|---|---|
| Starting material | 100 |
| pH 5.0 | 76 |
| pH 5.5 | 65 |
| pH 6.1 | 81 |
| pH 6.5 | 50 |
| pH 7.1 | 43 |
| pH 7.5 | 46 |
| pH 8.1 | 46 |
| pH 8.6 | 32 |

This series of experiments makes clear that the stabilization, particularly in the acid pH range, has markedly reduced the inactivation of the protease. The slight "breakthrough" at pH 5.5 can be explained by the fact that the isoelectric point of the protease is in this range. Na citrate prevents a loss of activity of >50% occurring in the preferred pH range.

EXAMPLE 13

The assay at pH 6.1 (Example 1) showed the best stabilization of the protease. Accordingly, different additives were tested at pH 6.0 and evaluated as described in Example 1:

The following final concentrations were set, with the concentration of the protease being 50 μg/ml:

50 mM Na citrate/50 mM NaCl, pH 6.0
0.75 g of sucrose/ml
100 mM glycine
100 mm arginine Results:

| Assay | Activity (%) |
|---|---|
| Starting material | 100 |
| Na citrate/NaCl | 54 |
| Na citrate/NaCl/sucrose | 85 |
| Na citrate/NaCl/sucrose/glycine | 92 |
| Na citrate/NaCl/sucrose/arginine | 97 |

Marked stabilization of the protease was demonstrated by adding sucrose and in each case one amino acid.

The invention claimed is:

1. A method for promoting hemostasis in a patient comprising administering to the patient an effective amount of a pharmaceutical preparation comprising a protease or a mixture of the protease and its proenzyme, wherein the protease
   a) activates blood clotting factor VII,
   b) is inhibited by the presence of aprotinin,
   c) is increased in its activity by the presence of at least one of the following: calcium ions, heparin, or heparin related substances, and
   d) in SDS-PAGE, on subsequent staining in the non-reduced state, comprises one or more bands in the molecular weight range from 50 to 75 kDa; and in SDS-PAGE, on subsequent staining in the reduced state, comprises a band at 40 to 55 kDa, one or more bands in the molecular weight range from 10 to 35 kDa, and a band, which corresponds to a proenzyme in the molecular weight range from 60 to 65 kDa.

2. A method for rapid wound closure comprising
   a) adding to at least one of a fibrin adhesive, fleece, or other release system an effective amount of the pharmaceutical preparation of claim 1; and
   b) applying said fibrin adhesive, fleece, or other release system to a wound.

3. A method for treating inborn or acquired deficiencies in the protease or proenzyme of claim 1, comprising administering to the patient an effective amount of the pharmaceutical preparation of claim 1.

4. A method for treating a patient suffering from hemophilia A, comprising administering to the patient an effective amount of the pharmaceutical preparation of claim 1.

5. A method for treating a patient who has developed antibodies against Factor VIII as a consequence of administration of Factor VIII, comprising administering to the patient an effective amount of the pharmaceutical preparation of claim 1.

6. The method of claim 1, wherein the pharmaceutical preparation is administered together with proenzyme activators.

7. The method of claim 2, wherein the pharmaceutical preparation is administered together with proenzyme activators.

8. The method of claim 3, wherein the pharmaceutical preparation is administered together with proenzyme activators.

9. The method of claim 4, wherein the pharmaceutical preparation is administered together with proenzyme activators.

10. The method of claim 5, wherein the pharmaceutical preparation is administered together with proenzyme activators.

11. The method of claim 2, wherein a hemorrhage is staunched.

12. A method for dissolution of fibrin-containing thrombi in a patient, comprising administering to the patient an effective amount of the pharmaceutical preparation of claim 1.

13. The method of claim 12, wherein the pharmaceutical preparation is administered together with a single or double chain plasminogen activator.

* * * * *